United States Patent [19]

Markwell et al.

[11] Patent Number: 4,755,525
[45] Date of Patent: Jul. 5, 1988

[54] 2-(FLUOROALKYL)-BENZIMIDAZOLES AS INHIBITORS OF 5-LIPOXYGENASE

[75] Inventors: Roger E. Markwell, Great Dunmow; Stephen A. Smith, Bishop's Stortford, both of England

[73] Assignee: Beecham Group p.l.c., Brentford, United Kingdom

[21] Appl. No.: 875,350

[22] Filed: Jun. 17, 1986

[30] Foreign Application Priority Data

Jun. 19, 1985 [GB] United Kingdom ............... 8515522

[51] Int. Cl.$^4$ .................. A61K 31/415; C07D 235/10
[52] U.S. Cl. .................... 514/394; 548/330; 548/332
[58] Field of Search ............... 548/332, 330; 514/394

[56] References Cited

U.S. PATENT DOCUMENTS 2,663,712  12/1953  Tulagin ..................... 548/330
3,528,798  9/1970   Pfeiffer .................... 548/332 X

FOREIGN PATENT DOCUMENTS

A0178413  4/1986   European Pat. Off. ......... 548/330
A1921911  2/1970   Fed. Rep. of Germany ....... 548/330

OTHER PUBLICATIONS

A. Beckett et al., *J. Pharm. Pharmacol.* 8, pp. 661–665 (1956).
P. Preston, *Chem. Reviews*, 74(3), p. 279–314 (1974).
R. Markwell, *J.C.S. Chem. Commun.*, pp. 428–430 (1979).
R. Vinegar et al., *Fed. Proc.*, 41, pp. 2588–2595 (1982).
V. Karsten et al., *Anal. Biochem.* 77, pp. 464–470 (1977).
B. Jakschik et al., *Biochem. Biophys. Res. Comm.*, 95 pp. 103–110 (1980).
Lane, E. et al., *J. Chem. Soc.*, 569 (1956).
*Chemical Abstracts*, 83:141692c (1975) [Flockhart, I. et al., *Proc. Eur. Soc. Study Drug Toxic.*, 1973, 14, 36–43].
*Chemical Abstracts*, 100:133915g (1984) [Adamson, G. et al., *Pestic. Sci.* 1984, 15(1), 31–39].
Hofmann, K., *Imidazole and its Derivatives*, Part 1, Interscience, New York, 1953, p. 261.

Primary Examiner—Richard A. Schwartz
Attorney, Agent, or Firm—James F. Haley, Jr.; Teresa L. Solomon

[57] ABSTRACT

A compound of the general formula I:

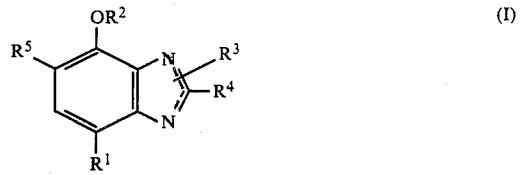

or a salt or solvate thereof, in which, $R^1$ represents hydrogen or a lower alkyl group,
$R^2$ represents hydrogen, a lower alkyl group, or

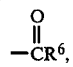

$R^3$ represents hydrogen, a lower alkyl group, or

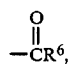

$R^4$ represents a lower alkyl group substituted by one or more fluorine atoms,
$R^5$ represents hydrogen, halogen or lower alkyl, and
$R^6$ represents a lower alkyl or a substituted or unsubstituted carbocyclic aryl group. The compounds are useful as inhibitors of 5-lipoxygenase.

12 Claims, No Drawings

2-(FLUOROALKYL)-BENZIMIDAZOLES AS INHIBITORS OF 5-LIPOXYGENASE

The present invention relates to benzimidazoles, processes for their manufacture, pharmaceutical preparations containing them, and their use in the treatment of various disorders.

It is known that certain arachidonic acid metabolites may produce harmful effects in man. For example, products produced via lipoxygenation of the acid, for example the leukotrienes, are implicated in the pathology of arthritis and inflammation, as well as in the production and the pathology of asthma and other allergic diseases. Accordingly, a compound capable of selectively inhibiting 5-lipoxygenase while having weaker inhibiting effects on the cyclo-oxygenase enzyme is beneficial by preventing the formation of inflammatory and bronchoconstrictor mediators while having little inhibitory effect on protective prostaglandins in the stomach or on the bronchodilatory cyclo-oxygenase products, for example, prostacyclin.

Further, products of the lipoxygenase pathway may adversely affect the integrity of the gastro-intestinal mucosa. Inhibition of lipoxygenase activity may lead to stimulation of cytoprotective prostaglandin production, particularly prostacyclin and PGE$_2$. This inhibition may therefore be of use in maintaining or establishing the integrity of the gastro-intestinal mucosa.

We have now found that certain benzimidazoles inhibit the 5-lipoxygenase enzyme, and accordingly the present invention provides a benzimidazole containing an optionally etherified or esterified hydroxy group in the 4-position and a fluorinated alkyl group in the 2-position.

The compounds of the invention find use in the treatment of inflammatory conditions, for example rheumatism and arthritis, in the treatment and prophylaxis of allergic conditions, for example bronchial asthma, rhinitis, hay fever and allergic eczema, and in the treatment of disorders related to loss of gastro-intestinal integrity, for example peptic ulcers, mucosal erosions and erosive gastritis.

U.S. Pat. No. 2,663,712, DE-OS No. 1921911 and J.C.S., [1956] 569 disclose certain benzimidazoles; there is, however, in none of these documents any suggestion of the possibility that any of the compounds disclosed may have any pharmaceutical use. Certain of these compounds were disclosed in J. Pharm. and Pharmacol 1956, 8, 661–5 and reported to have no significant antibacterial activity.

European published application No. EP-O 178 413-A published 23rd Apr. 1986, discloses a compound of the general formula A:

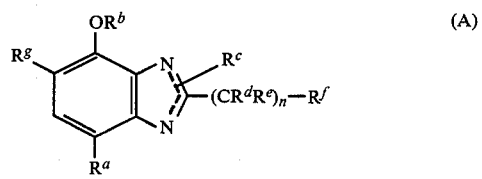

or a salt or solvate, e.g., hydrate, thereof, in which,
$R^a$ represents hydrogen or a lower alkyl group,
$R^b$ represents hydrogen, a lower alkyl group, or

$R^c$ represents hydrogen, a lower alkyl group, or

$R^d$ represents hydrogen or a lower alkyl group,
$R^e$ represents hydrogen or a lower alkyl group,
$R^f$ represents hydrogen, a lower alkyl, a substituted or unsubstituted aryl group, or —COOR$^i$,
$R^g$ represents hydrogen, halogen or lower alkyl,
$R^h$ represents a lower alkyl or a substituted or unsubstituted carbocyclic aryl group,
$R^i$ represents hydrogen or a lower alkyl, and n is 0 to 8, n being 0 when $R^f$ represents lower alkyl, as an active therapeutic substance.

More especially, the present invention provides a compound of the general formula I:

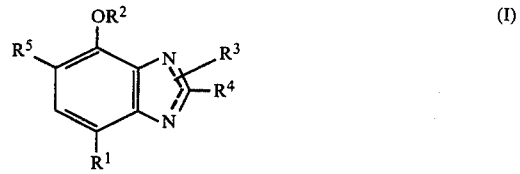

or a salt or solvate, e.g., hydrate, thereof, in which,
$R^1$ represents hydrogen or a lower alkyl group,
$R^2$ represents hydrogen, a lower alkyl group, or

$R^3$ represents hydrogen, a lower alkyl group, or

$R^4$ represents a lower alkyl group substituted by one or more fluorine atoms,
$R^5$ represents hydrogen, halogen or lower alkyl, and
$R^6$ represents a lower alkyl or a substituted or unsubstituted carbocyclic aryl group.

When used herein with reference to alkyl or alkoxy groups, the term "lower" means that the group contains up to 6 carbon atoms, preferably up to 4 carbon atoms. Alkyl radicals may have straight or branched chains, and may be, for example, methyl, ethyl, n-propyl, isopropyl, n-butyl, isobutyl or tert-butyl.

In formula I, the symbol

means that $R^3$ may be attached to either of the nitrogen atoms of the imidazole ring and that, when $R^3$ represents hydrogen, tautomerism exists; both tautomers are included within the scope of this invention. When $R^3$ does not represent hydrogen, the two compounds differ because of the asymmetry of the benzene ring substituents, and both compounds are included within the scope of this invention.

When $R^1$ represents a lower alkyl group, it is advantageously a methyl or a tert-butyl group. It is preferred that both $R^2$ and $R^3$ represent hydrogen; when either of them represents lower alkyl, it is advantageously the methyl group and when either of them represents

it is advantageous that $R^6$ represents methyl.

When $R^6$ represents aryl, the group may be a carbocyclic group, suitably

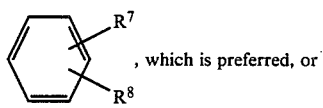

, which is preferred, or

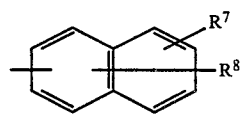

in which each $R^7$, $R^8$ independently represents hydrogen, hydroxy, lower alkoxy, e.g., methoxy, lower alkyl, e.g., methyl, or halogen, preferably chlorine or bromine. In the case of a substituted napthyl group the substituent, or each substituent independently if there are two, may be on either the linked ring or the non-linked ring.

When $R^5$ represents a halogen, chlorine is preferred; when it represents an alkyl group, tert-butyl is preferred.

$R^4$ is advantageously a trifluoromethyl group.

Within the compounds of formula I are a group of compounds of formula II:

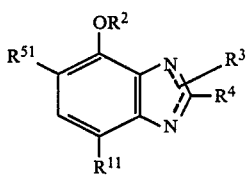

(II)

in which $R^{11}$ represents a lower alkyl group, $R^{51}$ represents hydrogen or a lower alkyl group and $R^2$, $R^3$ and $R^4$ are as defined in formula I.

Within the compounds of formula II are a group of compounds of formula IIa:

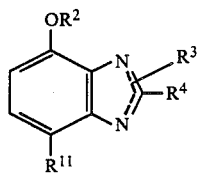

(IIa)

in which the variables have the meanings given above with reference to formula II.

Preferred values for the variables in formulae II and IIa are as described for the corresponding variables under formula I above.

The present invention further provides a compound of the general formula I or a pharmaceutically acceptable salt or solvate thereof for use as an active therapeutic substance.

The present invention also provides a physiologically tolerable compound of the general formula I, or a physiologically tolerable salt or solvate thereof, for use in treatment of the human or animal body.

The physiologically tolerable, or pharmaceutically acceptable salts of the compounds of formula I include acid addition salts with conventional acids such as hydrochloric, hydrobromic, boric, phosphoric, sulphuric and pharmaceutically acceptable organic acids such as acetic, tartaric, maleic, citric, succinic, benzoic, ascorbic, methanesulphonic, $\alpha$-keto-glutaric, $\alpha$-glycerophosphoric, and glucose-1-phosphoric acids. Preferably the acid addition salt is a hydrochloride.

The compounds of the formula I and their pharmaceutically acceptable salts may also form solvates with pharmaceutically acceptable solvates and the invention extends to these.

It will also be realised that salts of the compounds of the formula I which are not pharmaceutically acceptable may be useful as intermediates in the preparation of pharmaceutically acceptable salts of compounds of the formula I or the compounds of the formula I themselves, and as such form an aspect of the present invention.

In another aspect, the invention provides a pharmaceutical composition comprising a compound of formula I or a pharmaceutically acceptable salt or solvate thereof, together with a pharmaceutically acceptable carrier.

The present invention also provides a pharmaceutical preparation comprising a physiologically tolerable compound of the general formula I, or a physiologically tolerable salt or solvate thereof, in admixture or conjunction with a pharmaceutically acceptable carrier.

Preferably, a pharmaceutical preparation of the invention is in unit dosage form and in a form adapted for use in the medical or veterinarial fields. For example, such preparations may be in a pack form accompanied by written or printed instructions for use as an agent in the treatment of prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or preparation of the invention may be formulated for administration by any route, the preferred route depending upon the disorder for which treatment is required, and is preferably in unit dosage form or in a form that a human patient may administer to himself in a single dosage. Advantageously, the preparation is suitable for oral, rectal, topical, parenteral-intravenous or intramuscular administration or through the respiratory tract. Preparations may be designed to give slow release of the active ingredient.

Preparations may, for example, be in the form of tablets, capsules, sachets, vials, powders, granules, lozenges, reconstitutable powders, or liquid preparations, for example solutions or suspensions, or suppositories. Preparations which are especially suitable for administration to the respiratory tract and for topical administration are discussed in more detail below.

The preparations, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid preparations may be obtained by conventional methods of blending, filling tabletting or the like. Repeated blending operations may be used to distribute the active agent throughout those preparations employing large quantities of fillers. When the preparation is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating.

Preparations for oral administration as liquids may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, propylene glycol or ethyl alcohol, glycerine, water or normal saline; preservatives, for example methyl or propyl p-hydroxybenzoate or sorbic acid; and if desired conventional flavouring or colouring agents.

For parenteral administration, fluid forms are prepared utilizing the compound and a sterile vehicle, and, depending on the concentration used, may be either suspended or dissolved in the vehicle. In preparing solutions the compound may be dissolved in water for injection and filter sterilized before filling into a suitable vial or ampoule and sealing. Advantageously, adjuvants, for example a local anaesthetic, a preservative and buffering agents can be dissolved in the vehicle. To enhance the stability, the compositions can be frozen after filling into the vial and the water removed under vacuum. Parenteral suspensions are prepared in substantially the same manner, except that the compound is suspended in the vehicle instead of being dissolved, and sterilization is not accomplished by filtration. The compound may be sterilized by exposure to ethylene oxide before suspending in the sterile vehicle. Advantageously, a surfactant or wetting agent is included in the composition to facilitate uniform distribution of the compound.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For topical administration, the preparations may also be presented as an ointment, cream, lotion, gel, aerosol, or skin paint for topical application.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

For use in treatment of inflammatory diseases, a preparation of the invention will preferably be in a form suitable for oral administration, for example a tablet or capsule or a sachet containing reconstitutable powder. A unit dose will generally contain from 20 to 1000 mg and preferably will contain from 30 to 500 mg, in particular 50, 100, 150, 200, 250, 300, 350, 400, 450, or 500 mg. The preparation may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

For treatment of disorders related to the loss of gastro-intestinal integrity, a unit dose will normally contain 1 to 2000 mg, for example 5 to 1000 mg, of the active ingredient. Unit doses will normally be administered at least once a day, for example 1, 2, 3, 4, 5 or 6 times a day such that the total daily dose is normally in the range of 0.1 to 30 mg/kg body weight per day, e.g. 7 to 2000 mg/day for a 70 kg human adult.

For treatment of all the above-mentioned disorders, the compositions (preparations) may contain from 0.1% by weight to 99% by weight, preferably from 10 to 60% by weight, of the active ingredient, depending on the method of administration.

The present invention also provides a method of treatment which comprises administering a physiologically tolerable compound of the formula (I) or a physiologically tolerable salt thereof to a human or animal body.

The present invention further provides a method of treatment or prophylaxis of a disorder selected from the group consisting of inflammatory conditions, allergic conditions and loss of gastro-intestinal integrity in mammals which comprises administering to the sufferer an effective amount of a compound of formula I or a pharmaceutically acceptable salt or solvate thereof.

The present invention also provides a process for the manufacture of a compound of the formula I, wherein a compound of the formula IV:

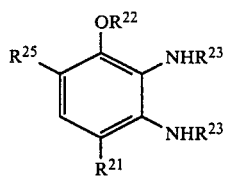
(IV)

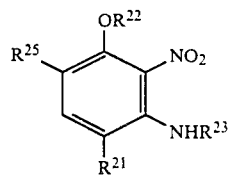
-continued wherein $R^{21}$ represents hydrogen or a lower alkyl group, or a group or atom convertible thereto, $R^{22}$ represents hydrogen, or a lower alkyl group, or a group or atom convertible thereto, one $R^{23}$ represents hydrogen and the other $R^{23}$ represents hydrogen or a lower alkyl group, or a group or atom convertible thereto, and wherein $R^{25}$ represents hydrogen, halogen, or alkyl, or a group or atom convertible thereto, is treated to introduce a group of the formula V:

(V)

wherein $R^{24}$ represents $R^4$ or a group convertible to $R^4$, wherein $R^4$, has the meaning given above with reference to formula I, to form a compound of the formula VI:

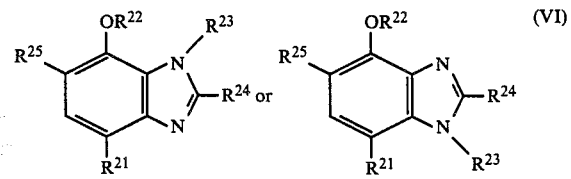
(VI)

and, if required, a nitrogen atom of, and/or the 4-oxygen atom on, the benzimidazole nucleus is acylated with a group of the formula

or is alkylated, and any required protective groups are removed, to form a compound of the formula I, optionally any group $R^1$, $R^2$, $R^3$, $R^4$ or $R^5$ is converted to other $R^1$, $R^2$, $R^3$, $R^4$ or $R^5$, and optionally a salt or solvate of the compound of formula I is formed.

The present invention also provides a process for the manufacture of a compound of the formula I wherein the compound of formula IV is obtained by reducing a compound of the formula VII:

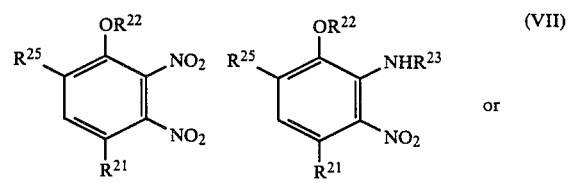
(VII)

wherein $R^{21}$, $R^{22}$ and $R^{23}$ and $R^{25}$ have the meanings given above in relation to formula IV, and if desired or required protective groups are removed to form the compound of the formula IV.

Compounds of the formula VII in which an $R^{23}$ group represents alkyl may be made, in the case of such an $R^{23}$ group meta to the $OR^{22}$ group, for example by nitration in the meta position, reduction of the nitro group, monoalkylating the amino group, and nitrating in the ortho position.

The compounds in which the alkyl $R^{23}$ group is ortho to the $OR^{22}$ group may be made, for example, by treating the ortho, meta dinitro compound with an amine of the formula $R^{23}NH_2$, which preferentially replaces the ortho nitro group.

Reduction of a compound of the formula VII may be effected by conventional chemical methods or preferably by catalytic methods. Catalytic reduction, using for example palladium on charcoal or Raney nickel, is conveniently effected in a conventional hydrogenation solvent, such as a lower alkanol, e.g., ethanol. When $R^{22}$ represents hydrogen, it may be protected by a benzyl group, introduced by, for example, heating with a benzyl halide/$K_2CO_3$/KI or NaI system in acetone or by a methyl group, introduced by $CH_3I$/$K_2CO_3$ in acetone.

Reaction of a compound of the formula IV, whether resulting from manufacture by reduction of a compound of the formula VII and, if desired or required, removal of protecting groups, or otherwise obtained, to introduce a group of the formula V, is preferably effected by heating with a compound of the formula VIII:

$$R^{24}COR^{32}$$ (VIII)

wherein $R^{32}$ represents a leaving group. For example the compound may be an acid, acid chloride, acid anhydride, including a mixed anhydride of the acid $R^{26}COOH$ and haloformate ester.

The presence of an acid catalyst, e.g., HCl, may be necessary, or the compound of formula VIII may itself be an acid. The reaction may be carried out in an inert solvent, or the compound of formula VIII may act as the solvent.

Further generally applicable methods of benzimadazole synthesis are described in *Chem Revs*, 1974, 74(3), 279.

Removal of protecting groups if desired or required may be effected by methods known per se, for example heating with HBr or aqueous hydrochloric acid to remove a methyl protecting group or catalytic hydrogenation to remove the benzyl group, using, for example, palladium/charcoal as catalyst.

The invention further provides a process in which one compound of the formula I is converted to another compound of the formula I.

The present invention in particular provides a process for preparing a compound of the formula I in which $R_3$ represents

which comprises treating a compound of the formula I in which $R^3$ represents H with an appropriate acylating agent. If $R^2$ represents hydrogen, it is desirably protected, as by a benzyl group, during the reaction. Advantageously, the reaction employs the appropriate acyl halide, preferably chloride, and is carried out in basic conditions using, for example, triethylamine and chloroform as the medium.

The present invention further provides a process for the manufacture of an ester of a compound of the formula I, which comprises acylating a compound of the formula I in which $R^2$ represents hydrogen, under conditions preventing or inhibiting acylation of the N-atoms of the benzimidazole nucleus, for example in a trifluoracetic acid medium, other reactive groups in the molecule being blocked by a protective group where necessary. The acylation preferably attaches a group of the formula

to the oxygen atom at the 2-position.

Compounds of the formula I in which $R^5$ is other than hydrogen may be made by methods known per se. For example, a compound where $R^5$ represents halogen, e.g., bromine or chlorine, may be prepared by halogenating phenol, if desired p-substituted as by alkyl, in the 2-position and then sequentially nitrating in the 5 and 6 positions, the phenolic hydrogen being protected at the required stages. A similar procedure may be used when $R^5$ represents an alkyl group; subsequent reduction to the diamino precursor of formula IV and its conversion to the benzimidazole of formula I may be effected as described above.

Reaction schemes for the preparation of 5-substituted benzimidazoles and of compounds of the formula VII in which one $R^{23}$ does not represent hydrogen are given below by way of illustration only. $R^1$, $R^{21}$, $R^{25}$ and $R^{24}$ have the meanings given above in relation to formula I, IV, IV and V respectively, $R^1$ preferably being methyl.

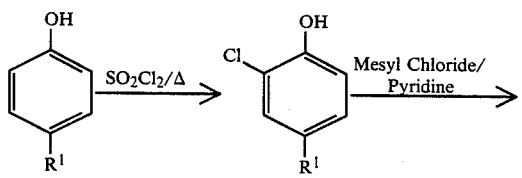

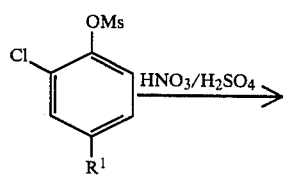

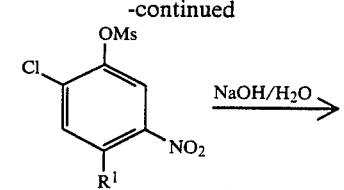

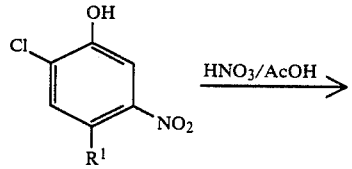

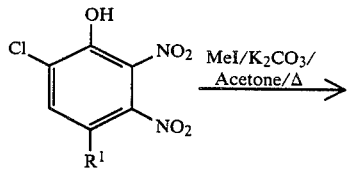

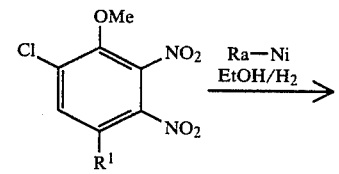

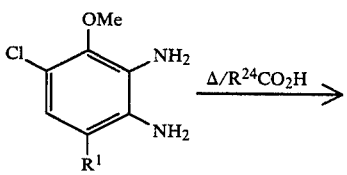

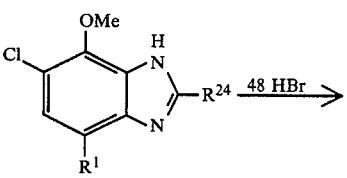

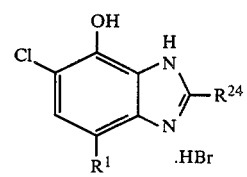

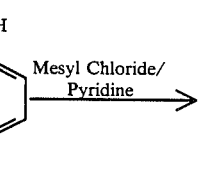

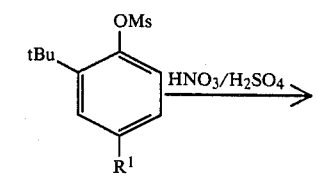

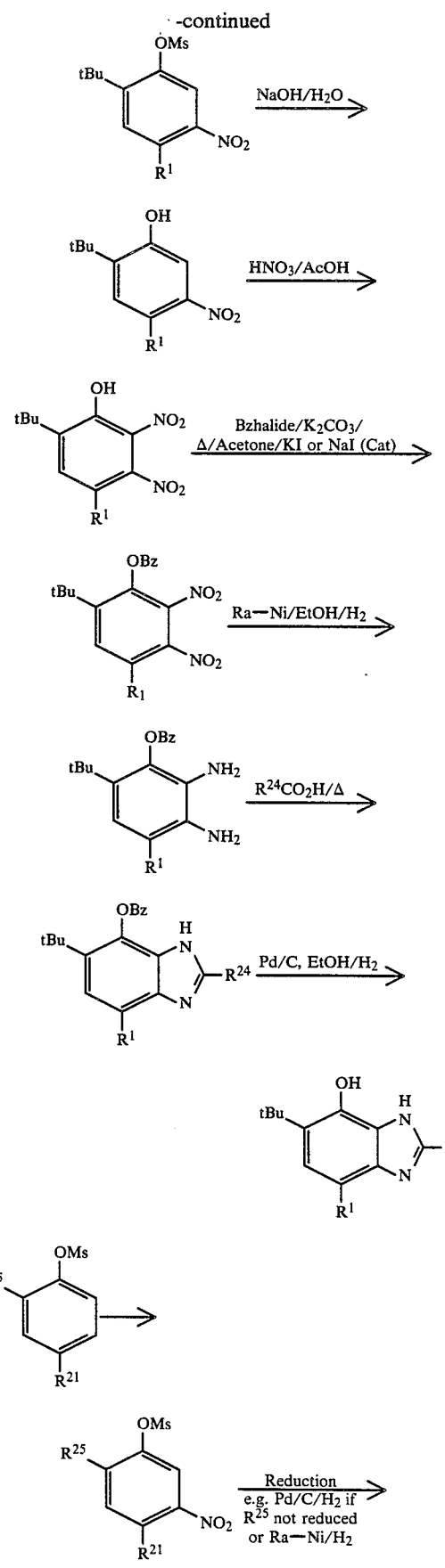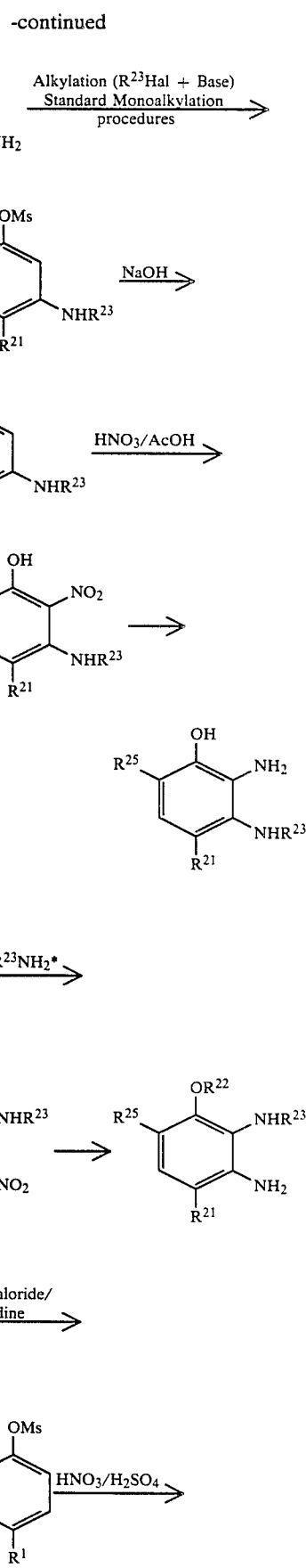

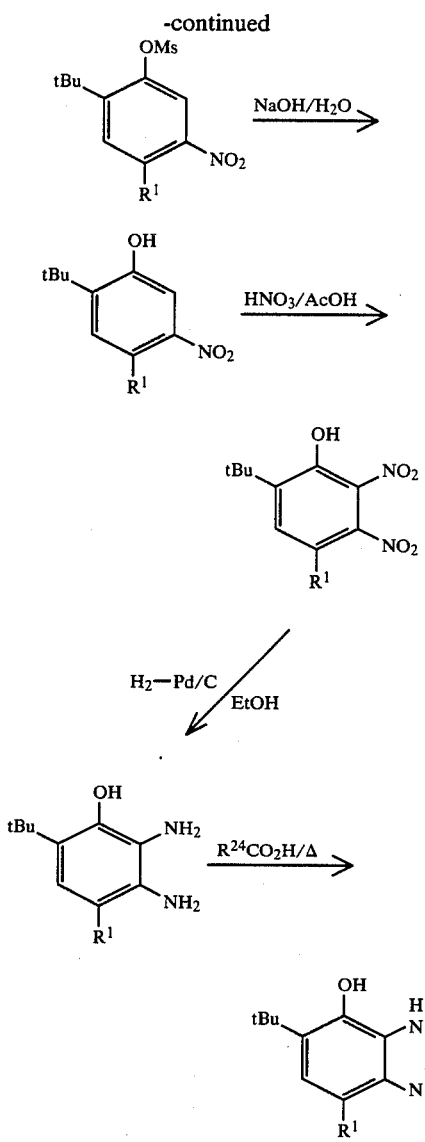

*see J. F. Bunnett and R. E. Zahler, Chem. Rev. 1951, 49, 354
R. E. Markwell, Chem. Commun. 1979, 428

The present invention also provides a process for the manufacture of a pharmaceutical preparation of a compound of the formula I, which comprises preparing a physiologically tolerable compound of the formula I, advantageously by the reaction of a compound of the formula IV with a compound of the formula VIII, the compound of the formula IV preferably having been made by reduction of the nitro groups in a compound of the formula VII to amine groups, and if required removing protecting groups, and if required forming a physiologically tolerable salt thereof, and admixing the physiologically tolerable compound or salt or solvate thereof with a pharmaceutically acceptable excipient (carrier).

The following descriptions illustrate the preparation of intermediates for the compounds of the invention. The following examples illustrate the invention:

DESCRIPTION 1

2-Nitro-4-hydroxy-5-tert-butyltoluene-O-mesylate

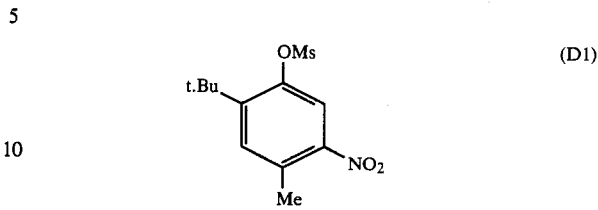

Mesyl chloride (147 g) was added dropwise over 0.5 h to a solution of 3-tert-butyl-4-hydroxytoluene (200 g) in pyridine (500 ml) at 0° C. The solution was stirred at 10° C. for 1 h and then at room temperature for a further 3 h. It was poured into excess 5N-hydrochloric acid and extracted with dichloromethane. The organic layer was washed with 5N-hydrochloric acid, water and dried ($Na_2SO_4$). Evaporation to dryness in vacuo afforded crude 3-tert-butyl-4-hydroxytoluene-O-mesylate (250 g) which was dissolved in concentrated sulphuric acid (750 ml) and cooled to 0° C. A mixture of concentrated nitric acid (93 g) and concentrated sulphuric acid (175 ml) was added dropwise over 1 h maintaining the temperature at 0° C. The solution was poured onto ice, and the resulting solid was collected, washed with water and air-dried to afford the title compound (260 g), m.p. 69°–78° C. sufficiently pure for the next step. A portion was recrystallised from chloroformpentane, m.p. 91°–92° C.

Anal: $C_{12}H_{17}NO_5S$ requires C, 50.16; H, 5.96; N, 4.87%. Found: c, 49.98; H, 5.98; N, 4.85%.

DESCRIPTION 2

2-Nitro-4-hydroxy-5-tert-butyltoluene

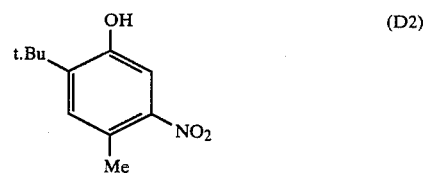

The crude product from Description 1 (260 g) was stirred with a solution of sodium hydroxide (130 g) in water (800 ml) at 60°–70° C. until all the solid had dissolved (1.5 h). The solution was filtered and poured onto an excess of ice and 5N-hydrochloric acid. The mixture was extracted with dichloromethane and the organic layer was washed with water and dried ($Na_2SO_4$). Evaporation to dryness in vacuo afforded the title compound (140 g) sufficiently pure for the next step.

A portion was recrystallised from dichloromethane-pentane, m.p. 96°–98° C.

Anal: $C_{11}H_{15}NO_3$ requires C, 63.4; H, 7.23; N, 6.69%. Found: C, 63.22; H, 7.2; N, 6.69%.

DESCRIPTION 3

2,3-Dinitro-4-hydroxy-5-tert-butyltoluene

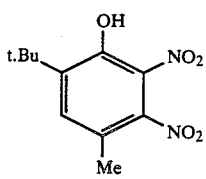
(D3)

A solution of fuming nitric acid (10.02 ml) in acetic acid (15 ml) was added dropwise over 15 min to a solution of the crude product from Description 2 (35 g) in acetic acid (60 ml) while maintaining the temperature at 18°-20° C. After a further 10 min the solution was poured onto ice and the resulting solid was collected and washed with water. It was dissolved in dichloromethane, washed with water and dried ($Na_2SO_4$). The product was purified by column chromatography on Silica Gel 60 (250 g) eluting with dichloromethane. Recrystallisation from dichloromethane-pentane afforded the title compound (25 g), m.p. 104°-105° C.

Anal: $C_{11}H_{14}N_2O_5$ requires C, 51.97; H, 5.55; N, 11.02%. Found: C, 51.88; H, 5.62; N, 11.00%.

DESCRIPTION 4

2,3-Diamino-4-hydroxy-5-tert-butyltoluene

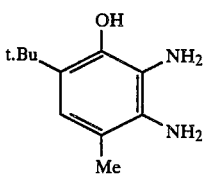
(D4)

A solution of 2,3-dinitro-4-hydroxy-5-tert-butyltoluene (Description 3) (7.5 g) in ethanol (350 ml) was hydrogenated at room temperature and atmospheric pressure over 10% palladium-carbon (2.5 g) until uptake of hydrogen ceased. The solution was filtered under nitrogen and evaporated to dryness in vacuo to afford the unstable title compound, m.p. 129°-136° C., which was used immediately for the next reaction.

The residue was re-crystallised from chloroform-hexane to afford the title compound (14.2 g), m.p. 100°-101° C.

EXAMPLE 1

5-tert-Butyl-4-hydroxy-7-methyl-2-trifluoromethylbenzimidazole

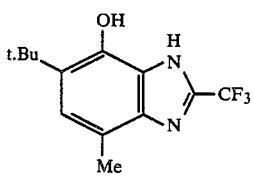
(E1)

A solution of 2,3-diamino-4-hydroxy-5-tert-butyltoluene (Description 4) (prepared from 5.5 g of 2,3-dinitro-4-hydroxy-5-tert-butyltoluene) in trifluoroacetic acid (39 ml) was heated under reflux, under nitrogen for 1 h. The solution was evaporated to dryness in vacuo and the residue was dissolved in chloroform and washed with 10% sodium carbonate, water, and dried ($Na_2SO_4$). The product was chromatographed on Silica Gel 60 (75 g) eluting with chloroform and later methanol-chloroform (1:9). The product was recrystallised from ether-pentane to afford the title compound 2.8 g, m.p. 140°-141° C.

Anal: $C_{13}H_{15}N_2OF_3$ requires C, 57,34; H, 5.5; N, 10.28%. Found: C, 57.33, H, 5.52; N, 10.28%.

EXAMPLE 2

4-Hydroxy-7methyl-2-trifluoromethylbenzimidazole hydrochloride hydrate (4:4:1)

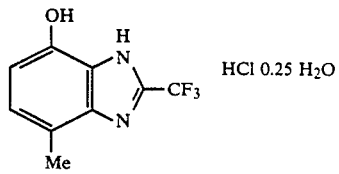

4-Benzyloxy-2,3-diaminotoluene (3.88 g, 17 mmol) prepared as described in European published application no. EP-O 178 413-A, Description 2, was heated under reflux in trifluoroacetic acid (25 ml) for 4 hours, the mixture was allowed to cool and evaporated to dryness in vacuo. The residue was partitioned between saturated aq. $NaHCO_3$ solution (100 ml) and $CH_2Cl_2$ (100 ml), the phases separated and the organic phase washed with $H_2O$ (100 ml). The dried organic phase ($MgSO_4$) was evaporated to dryness in vacuo to afford the 4-benzyloxy derivative of the title compound which was dissolved in EtOH (150 ml) and hydrogenated over 10% palladium on carbon at room temperature and pressure until hydrogen uptake ceased. The catalyst was removed by filtration, washed with EtOH and the combined filtrates acidified with hydrogen chloride gas. Removal of the solvent in vacuo afforded 1.52 g (41%) of the title compound m.p. 193°-4° C. (EtOH).

Anal: $C_9H_7F_3N_2O.HCl.0.25\ H_2O$ requires C, 42.03; H, 3.68; N, 10.71%. Found: C, 42.14; H, 3.33; N, 10.90%.

$^1H$ NHR (DMSO-$d_6$) δ 2.35 (3H, s) 6.65 (1H, d, J=8 Hz) 6.97 (1H, d, J=8 Hz) 8.53 (3H, br s, exchangeable with $D_2O$).

The pharmacological activity of illustrative compounds of this invention was determined using the following methods:

METHOD A

CARRAGEENIN-INDUCED PLEURISY IN THE RAT

This model of monocyte accumulation is based on the method of R. Vinegar, J. F. Truax, J. L. Selph and F. A. Voelker [Federation Proceeding 41, 2588-2595, 1982].

0.2 ml of a 2.0% solution of λ-carrageenin (Viscarin 402) in saline was injected intrapleurally in anaesthetised rats (wt. approx. 175-200 g). Compounds were administered 1 hour before carrageenin and at 24 and 48 hours after carrageenin. 72 hours after carrageenin injection, 4.0 ml of EDTA solution (5 g EDTA in 100 ml of 0.9% saline and 325 mg phenol red added together with saline to 1 liter) was injected intrapleurally after killing the animals, and the exudate removed with a syringe through the diaphragm. Exudate volume was measured spectrophotometrically (560 nm) and cellular content estimated with a DNA assay [Karsten U. and Wollenberger A. Anal. Biochem. 77, 464-470, 1977].

This test is used to indicate anti-inflammatory activity against carrageenin-induced pleurisy in the rat. The compound of Example 1 was active at a dose of 25 mg/kg (p.o.).

METHOD B

RBL-1 5-LIPOXYGENASE SCREEN

5-Lipoxygenase enzyme was prepared as a 10,000 g supernatant from RBL-1 cells by the method of Jakschik [Jakschik, B. A., F. F. Sun, L. M. Lee, and M. M. Steinhoff, 1980, Biochem. Biophys. Res. Comm. 95, 103]. The 10,000 g supernatant was diluted with homogenization buffer to the equivalent of $1.5-2.5 \times 10^7$ cells. $ml^{-1}$ and made 2 mM with respect to $CaCl_2$. Aliquots of 0.5 ml were then dispensed into tubes, and incubated at 29° C. with 5 μl ethanol or compound in ethanol at the desired concentration for 2 min. Then $[1-^{14}]$ arachidonic acid was added in buffer to give a final concentration of 6.3 μM and 0.2 μCi per incubation, and the reaction continued at 29° C. for 2 min. The reaction was terminated by adding 1 ml of acetone and cooling on ice, 0.5 ml of ice-cold saline and 10 μl of 2N formic acid were added, and the mixture was extracted with $2 \times 2$ ml of chloroform. The extract was stored under $N_2$ at −20° C. until analysis by chromatography. Activity was measured as the percentage of total radioactivity found in 5-HETE and 5,12-diHETE, and inhibition calculated as the decrease in formation of the sum of these two species in compound-treated incubates relative to control incubates.

This test is used to show inhibition of the 5-lipoxygenase enzyme in a mammalian RBL-1 cell free 5-lipoxygenase assay.

At a 100 mM concentration, the percentage inhibition by the compound of Example 1 was 18%, while at 1 μM the percentage inhibition was 93%. At a 20 μM concentration, the percentage inhibition by the compound of Example 2 was 68%.

We claim:

1. A compound of the formula

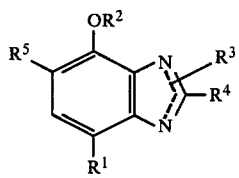

or a salt or solvate thereof, in which, $R^1$ represents hydrogen or a lower alkyl group, $R^2$ represents hydrogen, a lower alkyl group, or

$R^3$ represents hydrogen, a lower alkyl group, or

$R^4$ represents a lower alkyl group substituted by one or more fluorine atoms, $R^5$ represents hydrogen, halogen or lower alkyl, and $R^6$ represents a lower alkyl or a carbocyclic aryl group, which is selected from the group consisting of

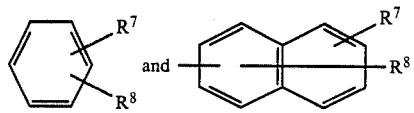

wherein each of $R^7$, $R^8$ is selected from the group consisting of hydrogen, hydroxy, lower alkoxy, and halogen and said compound being other than any one of the following:

$R^2$=acetoxy, $R^4$=trifluoromethyl and $R^1$, $R^3$ and $R^5$=hydrogen;

$R^2$=methyl, $R^4$=trifluoromethyl and $R^1$, $R^3$ and $R^5$=hydrogen, $R^2$=methyl, $R^4$=$C_3F_7$ and $R^1$, $R^3$ and $R^5$=hydrogen;

$R^4$=trifluoromethyl and $R^1$, $R^2$, $R^3$ and $R^5$=hydrogen;

$R^5$=chloro, $R^4$=trifluoromethyl; and $R^1$, $R^2$ and $R^3$=hydrogen;

$R^5$=chloro, $R^2$=methyl, $R^4$=trifluoromethyl and $R^1$ and $R^3$=hydrogen.

2. A compound according to claim 1 of the formula II:

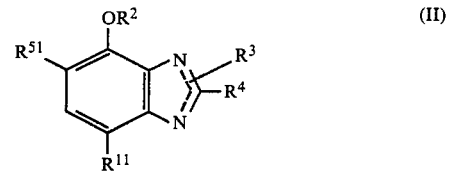

in which $R^{11}$ represents a lower alkyl group, $R^{51}$ represents hydrogen or a lower alkyl group and $R^2$, $R^3$ and $R^4$ are as defined in claim 1.

3. A compound according to claim 1 in which $R^1$ is methyl.

4. A compound according to claim 1 in which $R^5$ is hydrogen or tert-butyl.

5. A compound according to claim 1 in which $R^4$ is trifluoromethyl.

6. A compound according to claim 1 in which $R^2$ is hydrogen.

7. A compound according to claim 1 in which $R^3$ is hydrogen.

8. 5-tert-Butyl-4-hydroxy-7-methyl-2-trifluoromethyl benzimidazole or 4-hydroxy-7-methyl-2-trifluoromethyl benzimidazole, or a pharmaceutically acceptable salt or solvate thereof.

9. A pharmaceutical composition for treatment or prophylaxis of inflammatory conditions, allergic conditions and disorders related to the loss of gastro-intestinal integrity comprising an effective amount of a compound according to claim 1 or a pharmaceutically acceptable salt or solvate thereof, together with a pharmaceutically acceptable carrier.

10. A method of treatment or prophylaxis of inflammatory conditions in mammals, which comprises administering to the sufferer an effective amount of a compound according to claim 1 or a pharmaceutically acceptable salt or solvate thereof.

11. A method of treatment or prophylaxis of allergic conditions in mammals which comprises administering an effective amount of a compound according to claim 1 or a pharmaceutically acceptable salt or solvate thereof.

12. A method of treatment or prophylaxis of loss of gastrointestinal integrity in mammals which comprises administering an effective amount of a compound according to claim 1 or a pharmaceutically acceptable salt or solvate thereof.

* * * * *